US008309610B2

(12) United States Patent
Gruss et al.

(10) Patent No.: US 8,309,610 B2
(45) Date of Patent: Nov. 13, 2012

(54) CRYSTALLINE FORMS OF (1RS,3RS,6RS)-6-DIMETHYLAMINOMETHYL-1-(3-METHOXYPHENYL)CYCLOHEXANE-1,3-DIOL HYDROCHLORIDE

(75) Inventors: Michael Gruss, Aachen (DE); Helmut Buschmann, San Just Desvem Barcelona (ES); Andreas Fischer, Huertgenwald (DE); Wolfgang Hell, Aachen (DE); Dagmar Lischke, Eschweiler (DE)

(73) Assignee: Gruenenthal GmbH, Aachen (DE)

( * ) Notice: Subject to any disclaimer, the term of this patent is extended or adjusted under 35 U.S.C. 154(b) by 1109 days.

(21) Appl. No.: 11/885,039

(22) PCT Filed: Feb. 21, 2006

(86) PCT No.: PCT/EP2006/001548
§ 371 (c)(1),
(2), (4) Date: Jun. 6, 2008

(87) PCT Pub. No.: WO2006/089708
PCT Pub. Date: Aug. 31, 2006

(65) Prior Publication Data
US 2011/0306673 A1    Dec. 15, 2011

(30) Foreign Application Priority Data

Feb. 25, 2005 (DE) .......................... 10 2005 009 217
Feb. 25, 2005 (EP) ..................................... 05004183

(51) Int. Cl.
*A61K 31/135*     (2006.01)
*C07C 213/10*     (2006.01)
*A61P 25/22*      (2006.01)

(52) U.S. Cl. ........ 514/646; 514/506; 514/546; 514/620; 514/349; 514/369; 514/445; 564/305; 564/455; 564/443; 560/39; 558/70; 546/300

(58) Field of Classification Search .................. 514/646, 514/506, 546, 620, 349, 369, 445; 564/305, 564/455, 443; 560/39; 558/70; 546/300
See application file for complete search history.

(56) References Cited

U.S. PATENT DOCUMENTS

| 5,733,936 A | 3/1998 | Buschmann et al. |
| RE37,355 E | 9/2001 | Buschmann et al. |
| 2006/0121113 A1 | 6/2006 | Bartholomaeus |

FOREIGN PATENT DOCUMENTS

| EP | 0 753 506 B1 | 1/1997 |
| WO | WO 2005/009329 A2 | 2/2005 |

OTHER PUBLICATIONS

Berge et al., Journal of pharmaceutical sciences, Jan. 1977, vol. 6 (1) pp. 1-19.*
International Search Report dated Apr. 10, 2006 (Two (2) pages.).
PCT/IB/373 and PCT/ISA/237 (Nine (9) pages.).

* cited by examiner

*Primary Examiner* — Savitha Rao
(74) *Attorney, Agent, or Firm* — Crowell & Moring LLP

(57) ABSTRACT

This invention relates to solid crystalline forms of (1RS,3RS,6RS)-6-Dimethylaminomethyl-1-(3-methoxy-phenyl)cyclohexane-1,3-diol hydrochloride (1), methods of producing 1, methods of use of 1, use of 1 as analgesics and pharmaceutical compositions comprising 1.

41 Claims, 10 Drawing Sheets

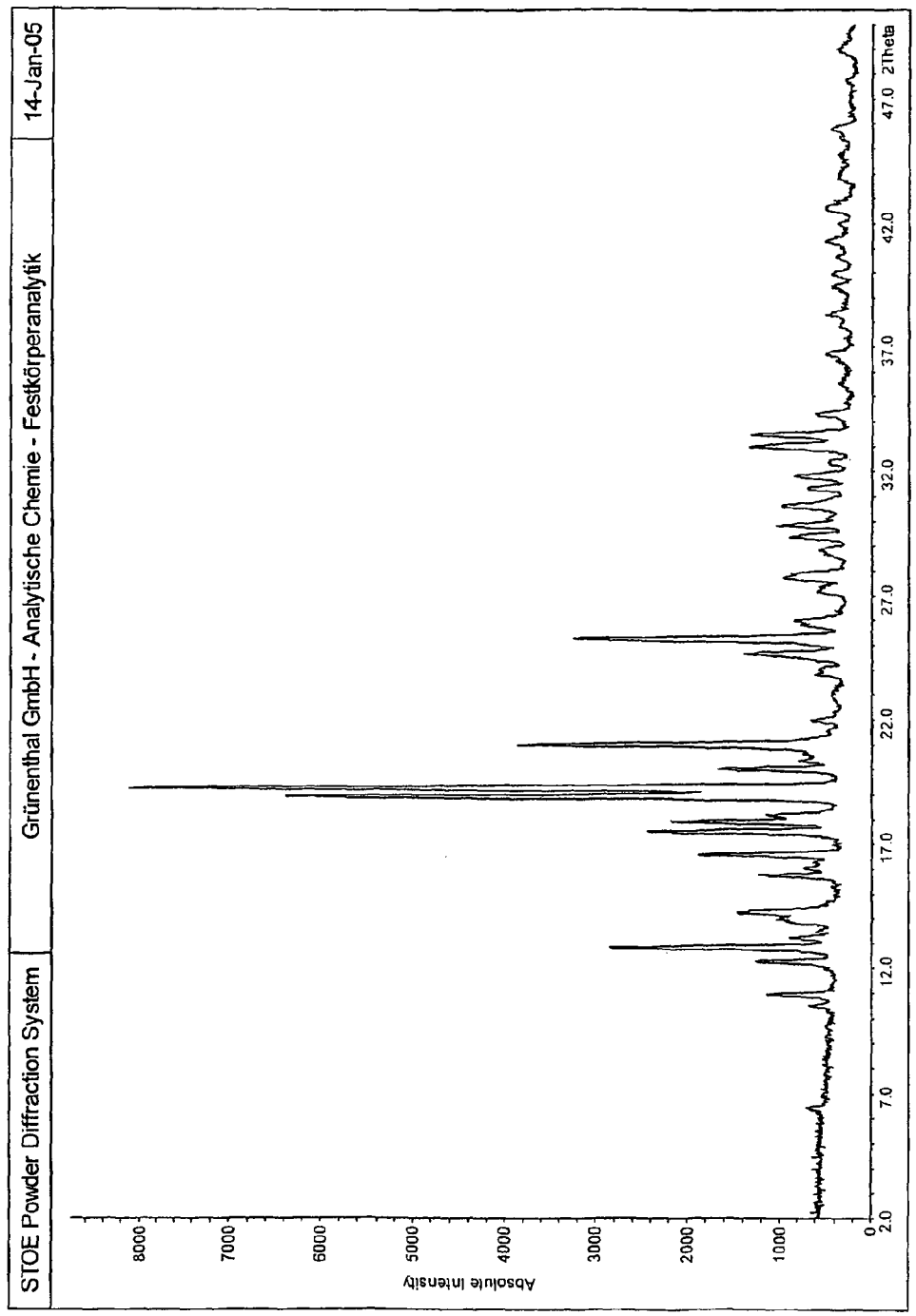
Figure 1 X-ray powder diffraction pattern of form A

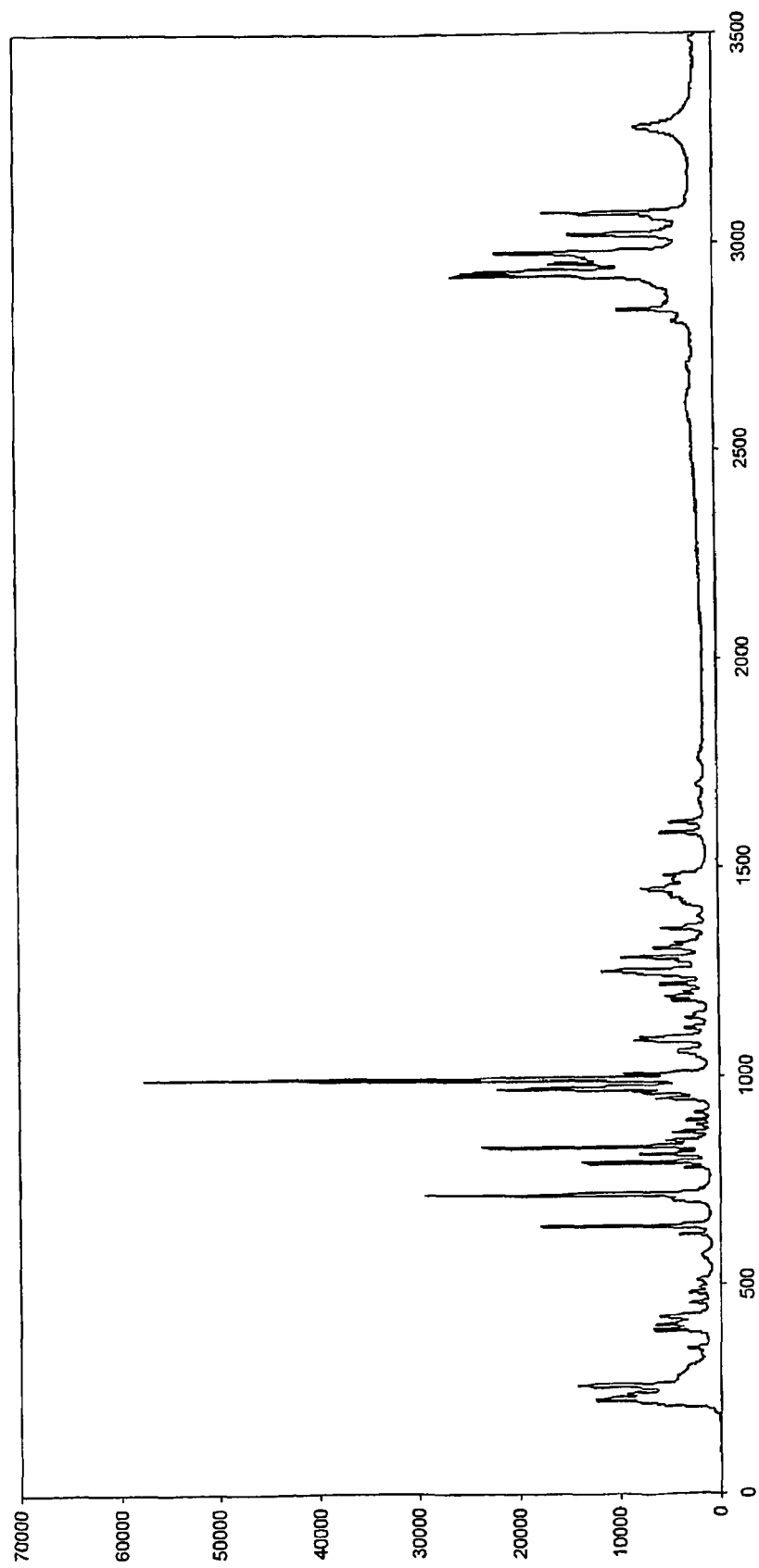
Figure 2 Raman Spectrum of form A

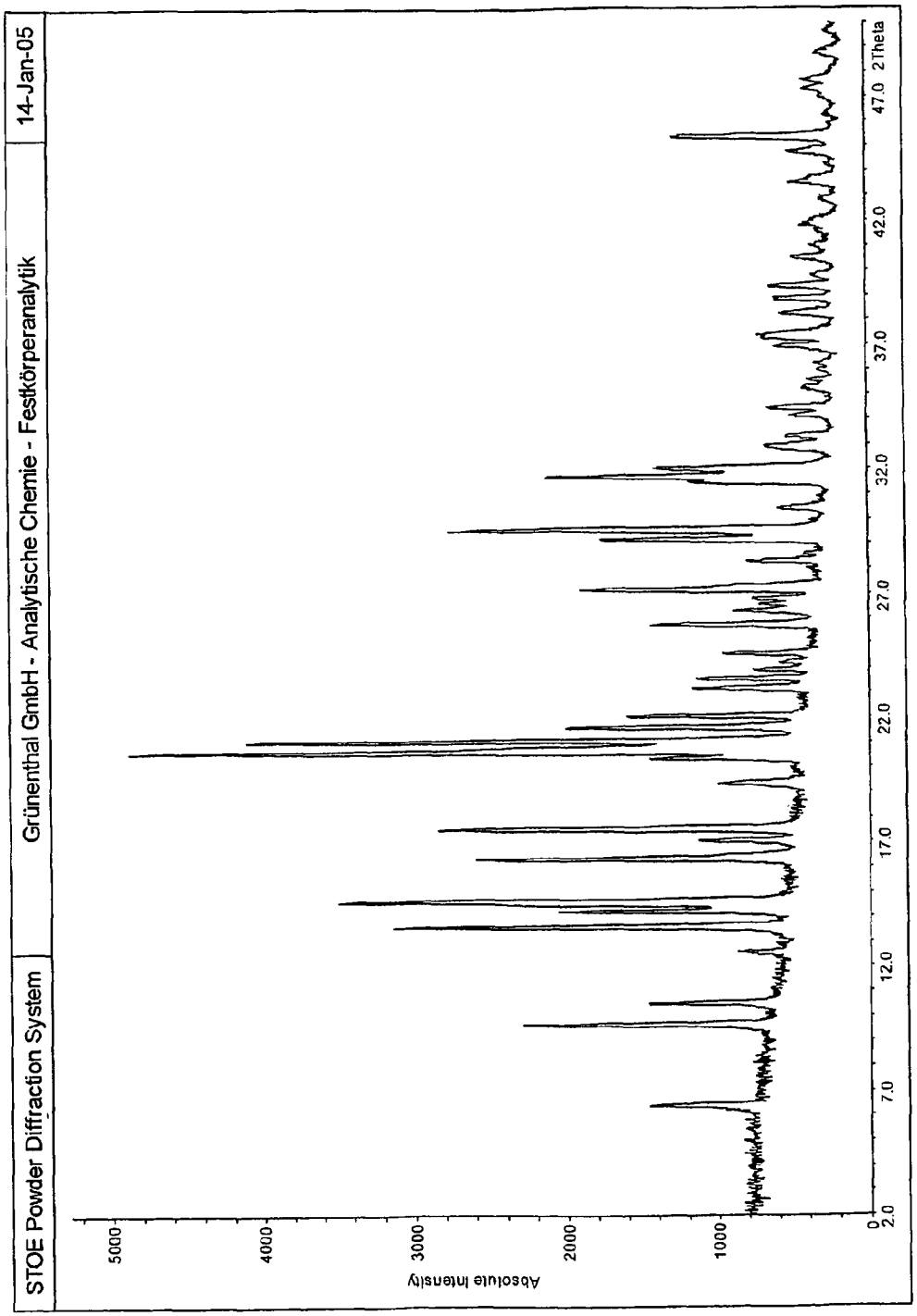
Figure 3 X-ray powder diffraction pattern of form B

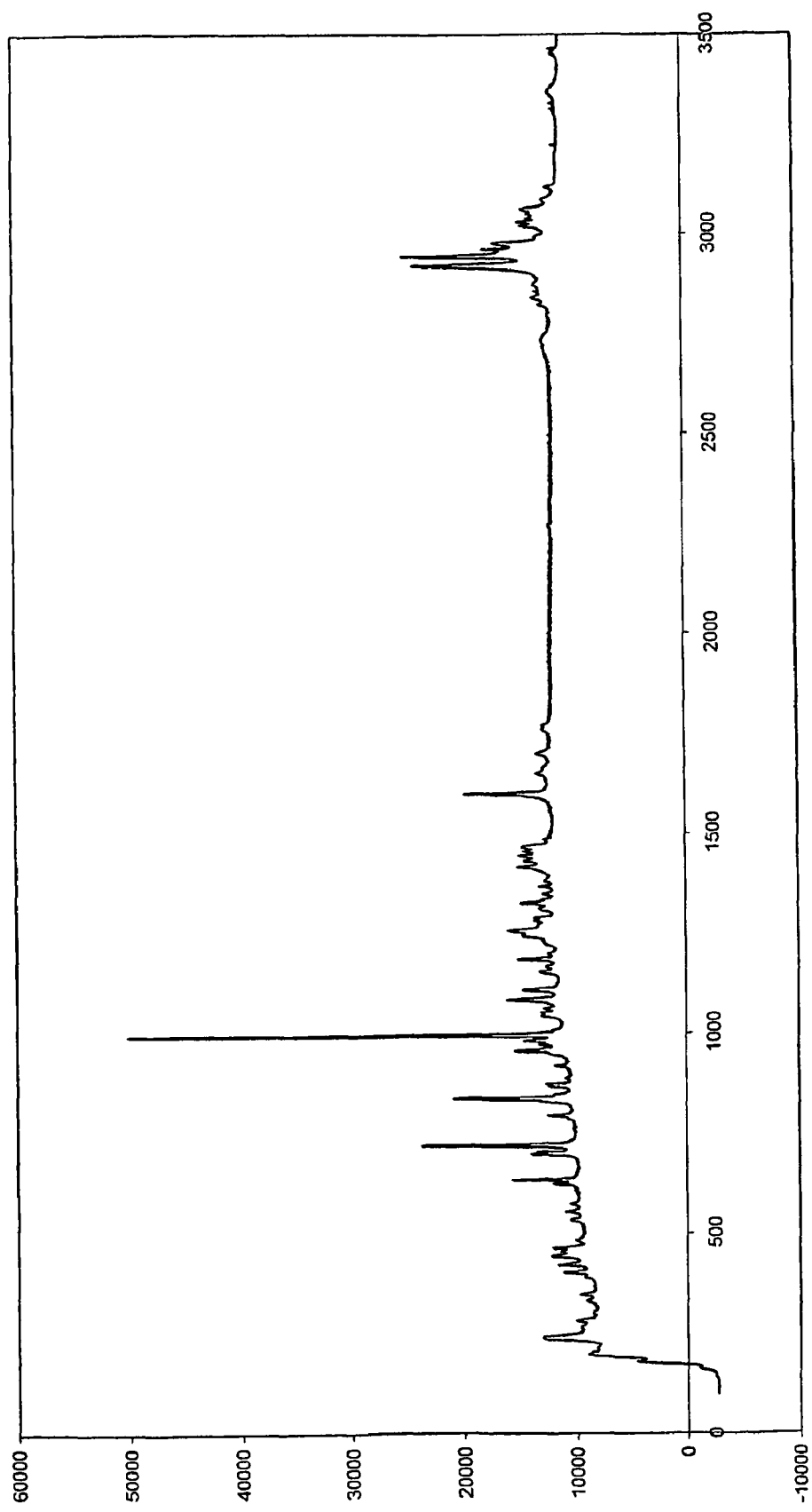
Figure 4 Raman Spectrum of form B

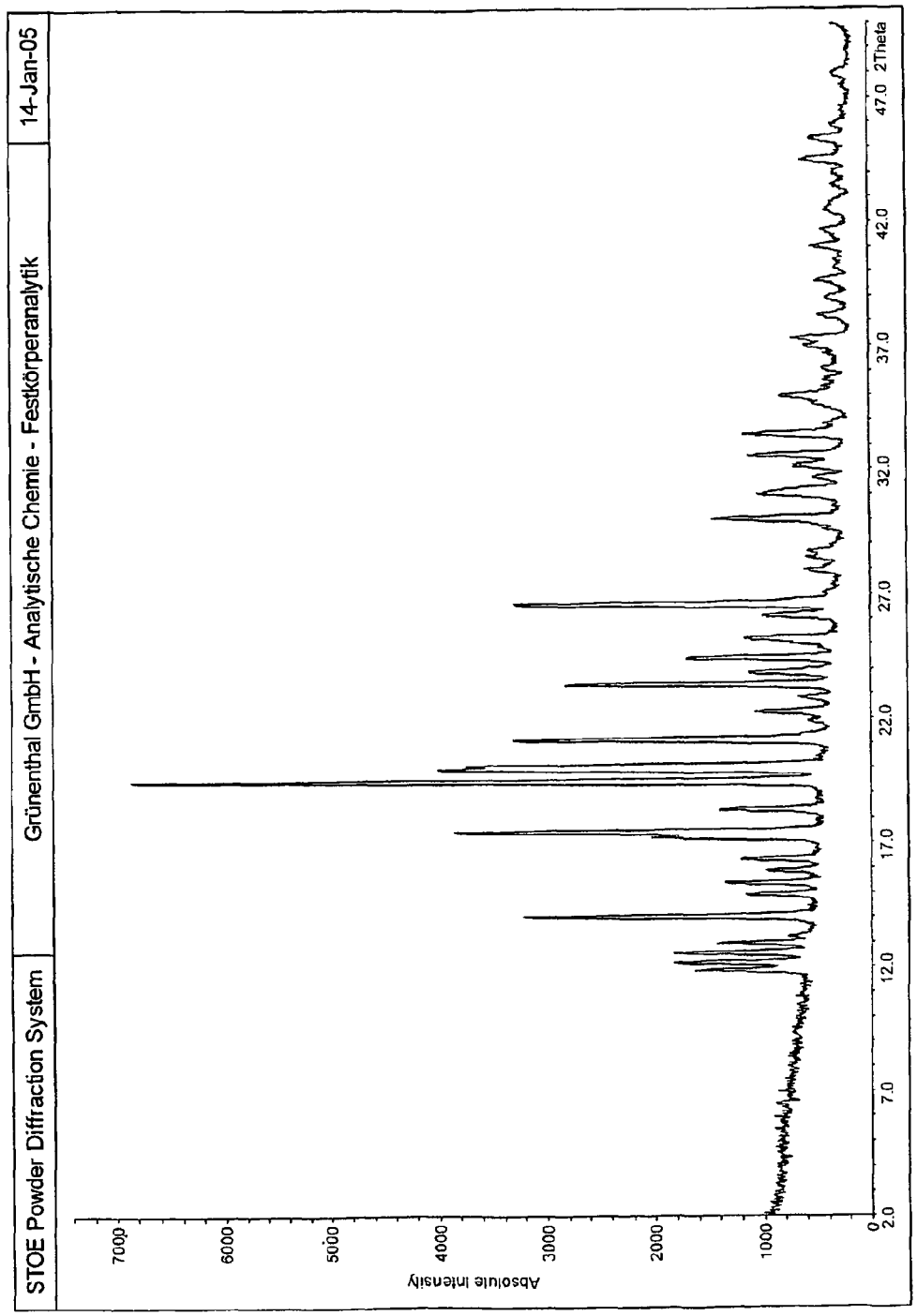
Figure 5 X-ray powder diffraction pattern of form C

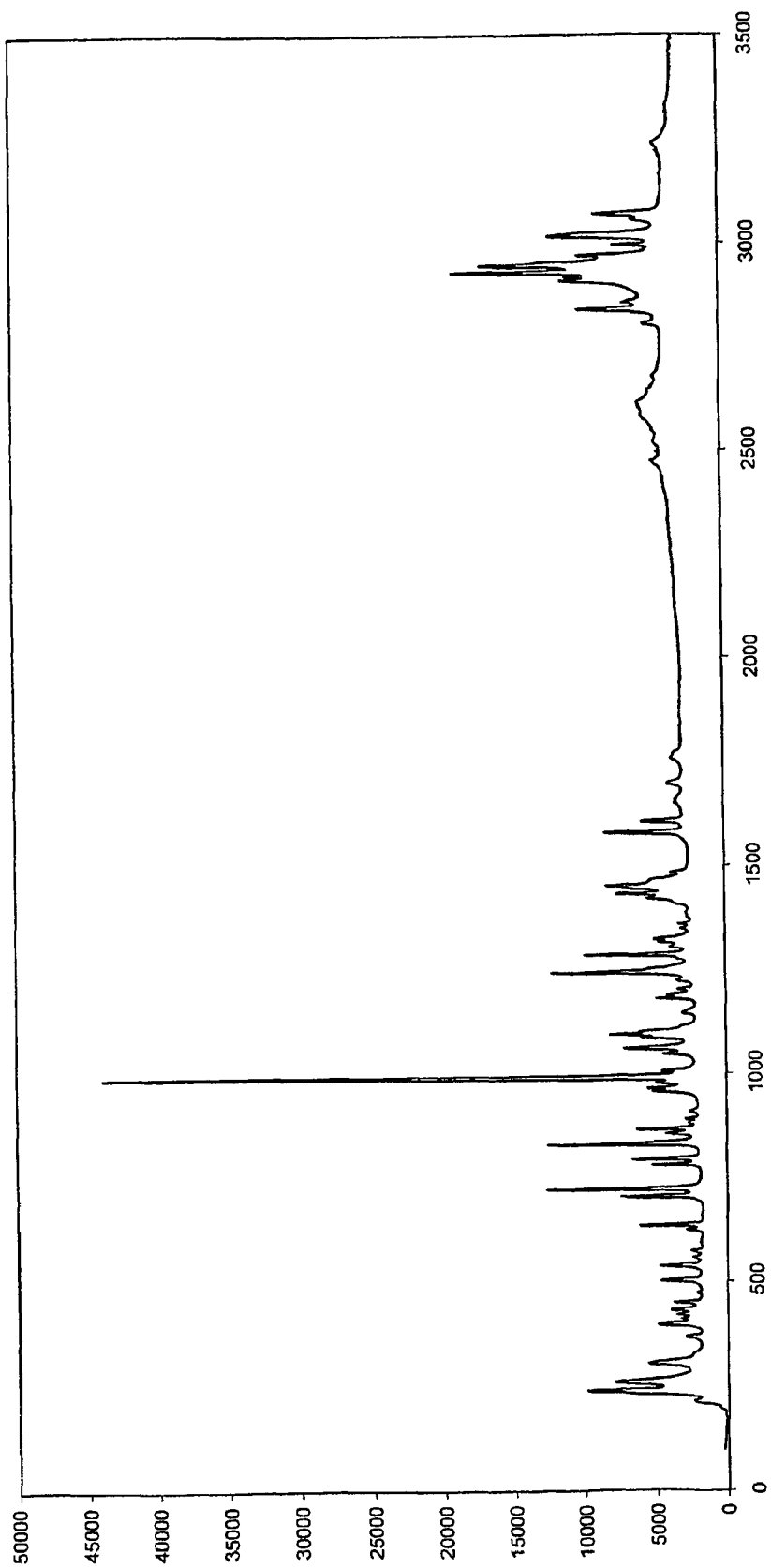
Figure 6 Raman Spectrum of form C

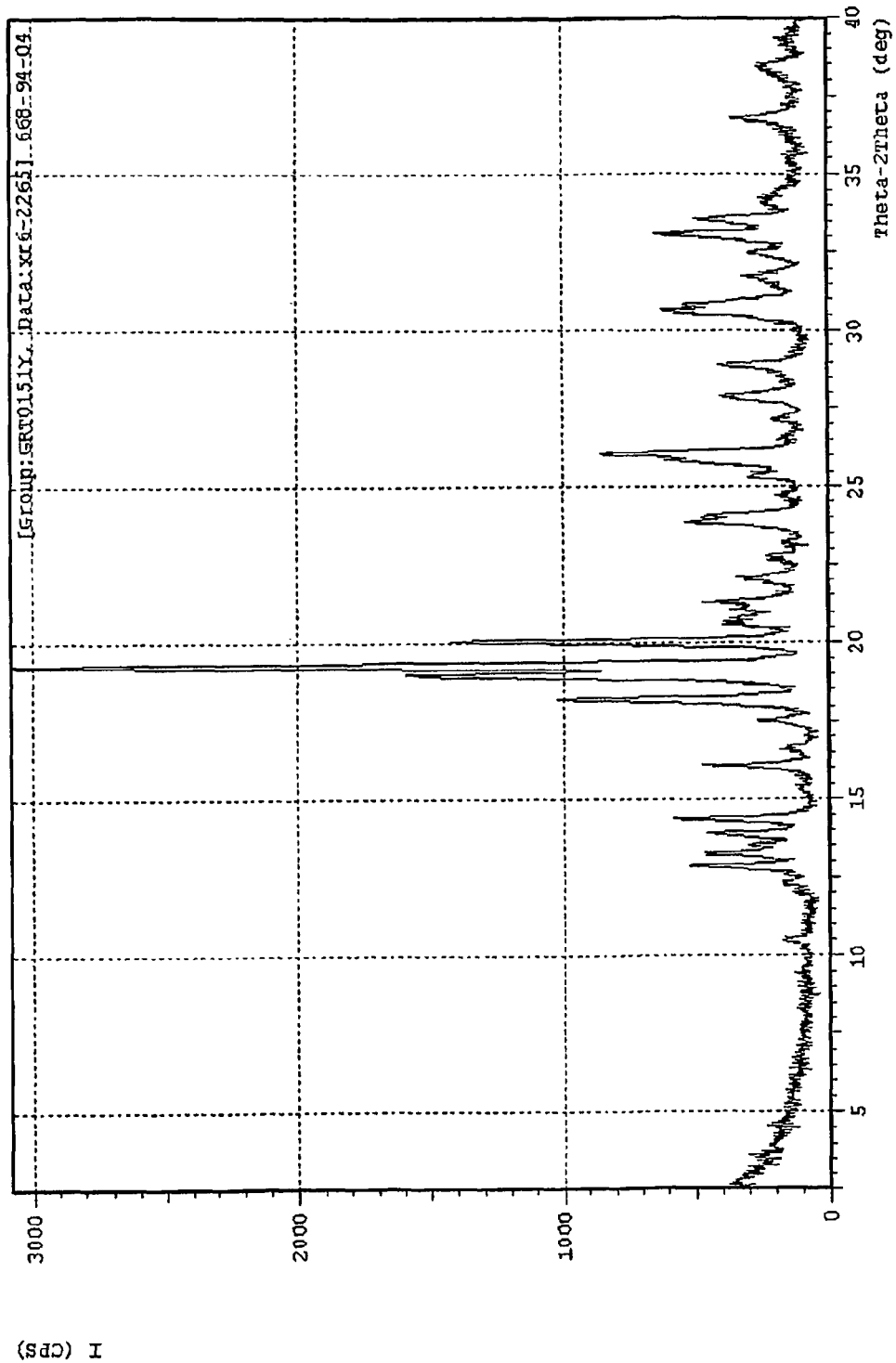
Figure 7 X-ray powder diffraction pattern of form D

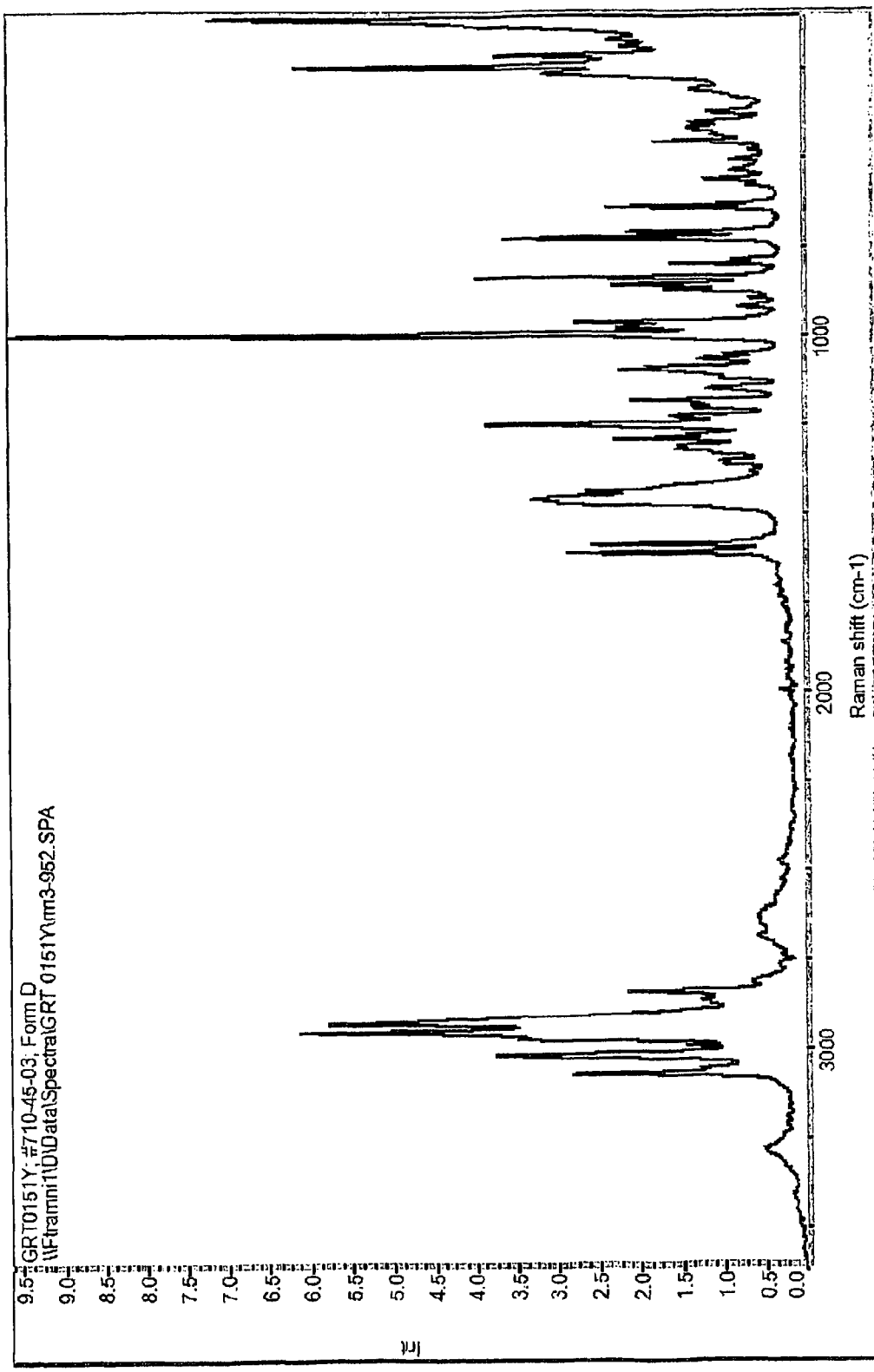

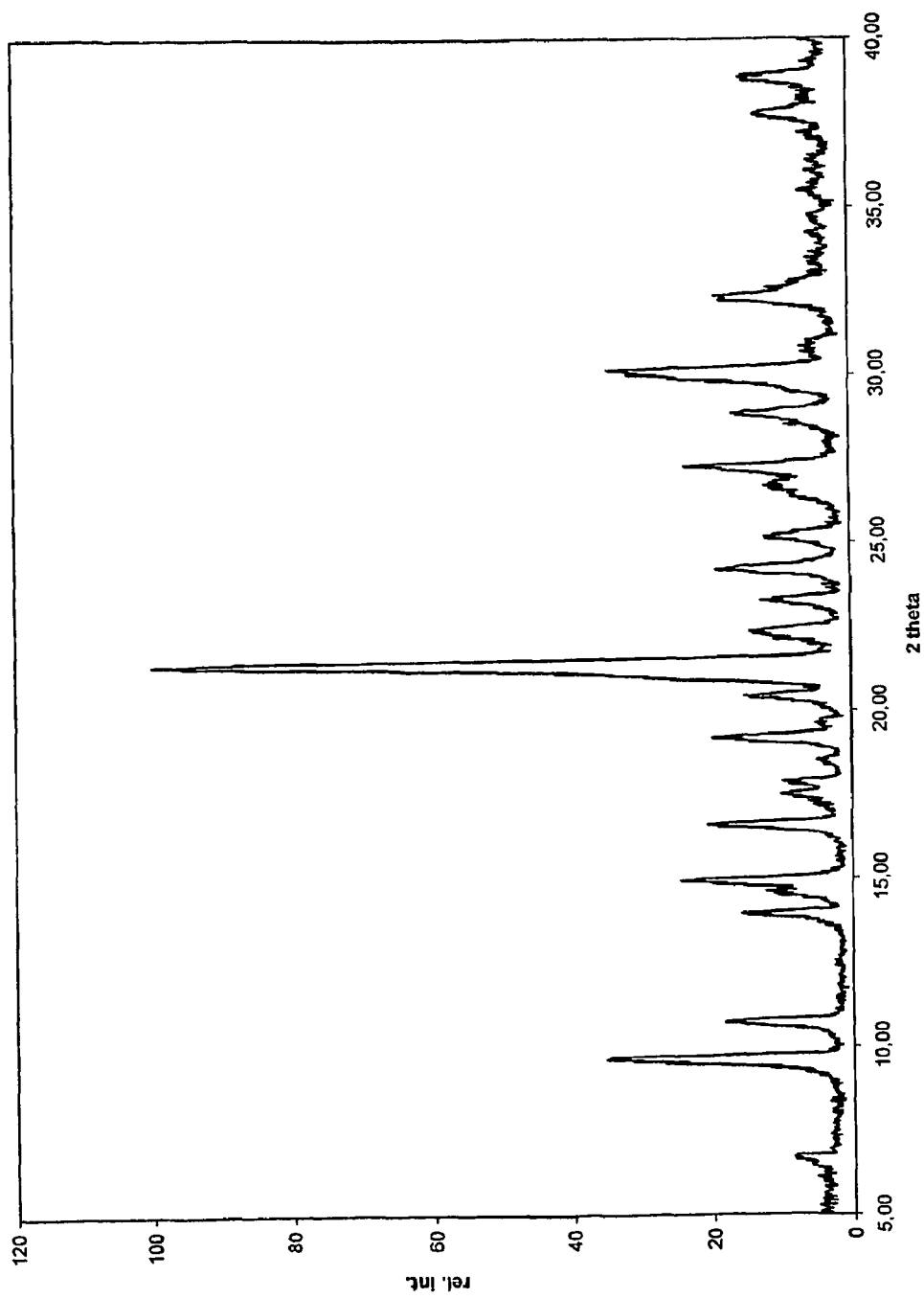
Figure 9 X-ray powder diffraction pattern of form E

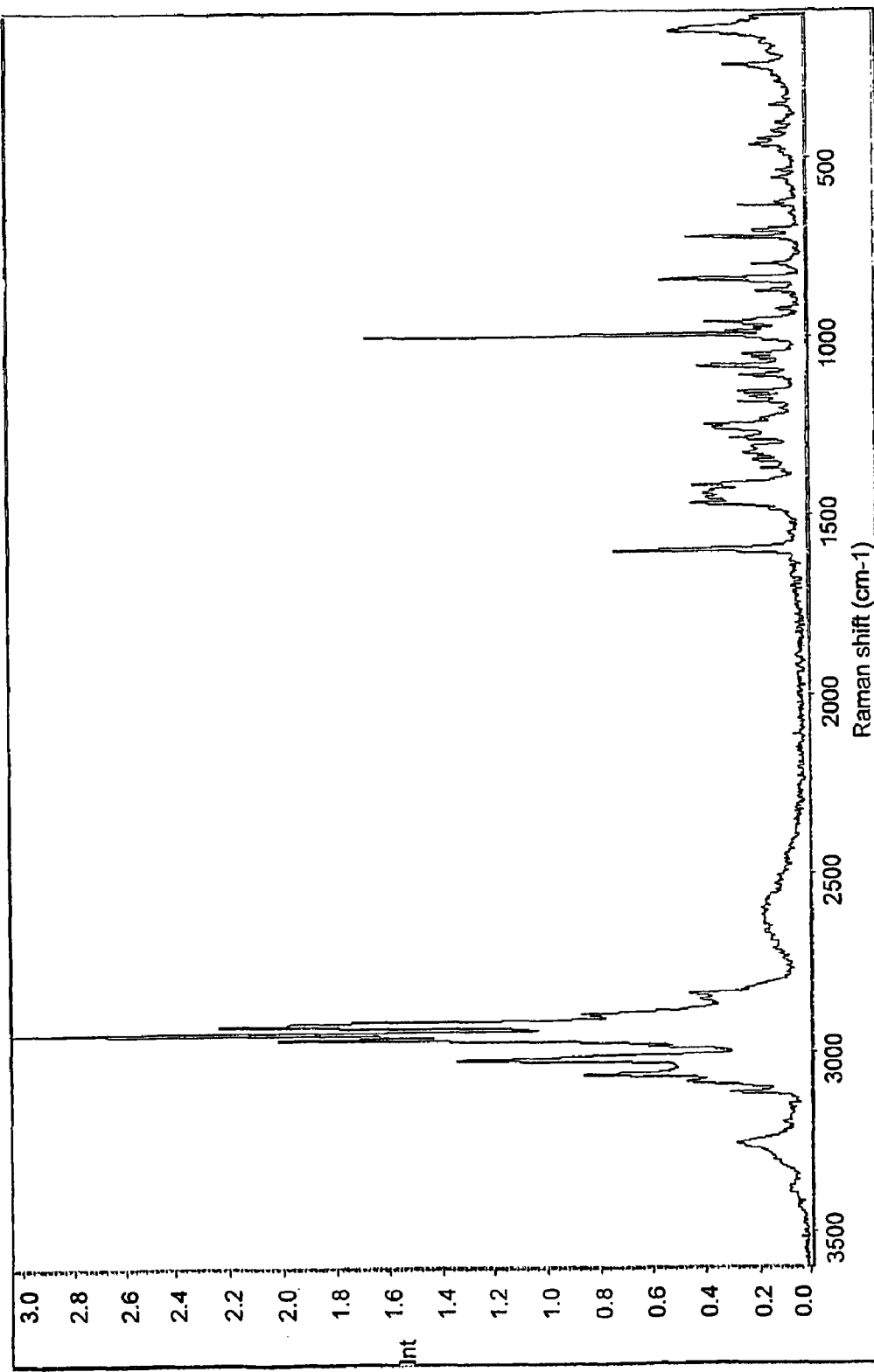

CRYSTALLINE FORMS OF (1RS,3RS,6RS)-6-DIMETHYLAMINOMETHYL-1-(3-METHOXYPHENYL)CYCLOHEXANE-1,3-DIOL HYDROCHLORIDE

This invention relates to solid crystalline forms of (1RS,3RS,6RS)-6-Dimethylaminomethyl-1-(3-methoxy-phenyl)cyclohexane-1,3-diol hydrochloride (1), methods of producing 1, methods of use of 1, use of 1 as analgesics and pharmaceutical compositions comprising 1.

The treatment of pain conditions is of great importance in medicine. There is currently a world-wide need for additional pain therapy. The pressing requirement for a target-oriented treatment of pain conditions which is right for the patient, which is to be understood as the successful and satisfactory treatment of pain for the patients, is documented in the large number of scientific works which have recently and over the years appeared in the field of applied analgesics or on basic research on nociception.

The underlying object of the present invention was to find new solid forms of (1RS,3RS,6RS)-6-Dimethylaminomethyl-1-(3-methoxy-phenyl)cyclohexane-1,3-diol hydrochloride, preferably useful in the treatment of pain.

U.S. Pat. Nos. RE 37355 E and 5,733,936 as well as European Patent EP 753 506 B1 disclose the substance and the synthesis of (1RS,3RS,6RS)-6-Dimethylaminomethyl-1-(3-methoxy-phenyl)cyclohexane-1,3-diol hydrochloride in example 18.

It has now been surprisingly found that (1RS,3RS,6RS)-6-Dimethylaminomethyl-1-(3-methoxy-phenyl)cyclohexane-1,3-diol hydrochloride can be produced in several different crystalline forms. The present invention provides the new forms form A, form B, form C, form D and form E of (1RS,3RS,6RS)-6-Dimethylaminomethyl-1-(3-methoxy-phenyl)cyclohexane-1,3-diol hydrochloride. These new forms of (1RS,3RS,6RS)-6-Dimethylaminomethyl-1-(3-methoxy-phenyl)cyclohexane-1,3-diol hydrochloride are useful for producing pharmaceutical compositions. It is the first time to have access to the relevant polymorphs of this important pharmaceutical compound. The polymorph forms are important for evaluation of synthesis, stability and safety both of this compound and of the pharmaceutical formulation made from this compound. Furthermore each of the polymorph forms are important in terms of the different pharmaceutical formulation process that might be involved, in which each of the polymorphs are advantageous with their special physicochemical properties.

The compound (1RS,3RS,6RS)-6-Dimethylaminomethyl-1-(3-methoxy-phenyl)cyclohexane-1,3-diol has the following structure:

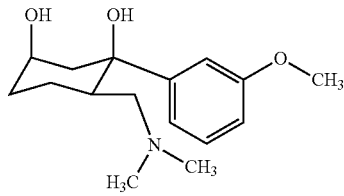

oder in a different notation:

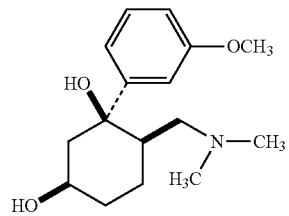

The new crystalline forms can be identified by X-ray powder diffraction. The X-ray powder diffraction ("XRPD") patterns are shown in FIG. 1, FIG. 3, FIG. 5, FIG. 7 and FIG. 9 with the peak listing shown in Table 1. Ambient temperature and room temperature is defined as 23±3° C.

The most important X-ray lines (2-theta values) in terms of intensity characterizing form A of (1RS,3RS,6RS)-6-Dimethylaminomethyl-1-(3-methoxy-phenyl)cyclohexane-1,3-diol hydrochloride showing one or a combination of the following in a powder diffraction measurement when measured using Cu Kα radiation at ambient temperature are 12.9±0.2, 17.5±0.2, 19.0±0.2, 19.3±0.2, 21.0±0.2 and 25.3±0.2.

To discriminate crystalline form A of (1RS,3RS,6RS)-6-Dimethylaminomethyl-1-(3-methoxy-phenyl)cyclohexane-1,3-diol hydrochloride from the other forms it is more advantageous to look at the unique peaks in the X-ray diffraction diagram, i.e. the lines with sufficient intensity at 2-theta values, where the other modifications do not show lines with significant intensity. Such characteristic X-ray lines (2-theta values) for form A in a powder diffraction pattern when measured using CuKα radiation at ambient temperature are: 11.0±0.2, 12.3±0.2, 12.9±0.2, 16.6±0.2, 17.9±0.2, 19.0±0.2 and 25.3±0.2.

RAMAN technique can also be used to identify the crystalline form A of (1RS,3RS,6RS)-6-Dimethylaminomethyl-1-(3-methoxy-phenyl)cyclohexane-1,3-diol hydrochloride as shown in FIG. 2. The most important Raman wave numbers (cm$^{-1}$) in terms of intensity characterizing form A of (1RS,3RS,6RS)-6-Dimethylaminomethyl-1-(3-methoxy-phenyl)cyclohexane-1,3-diol hydrochloride showing one or a combination of the following in a Raman spectrum when measured using a laser wave length of 632 nm are 227±4, 262±4, 643±4, 716±4, 813±4, 830±4, 970±4, 993±4, 1252±4, 2973±4 and 3273±4 cm$^{-1}$.

In another aspect the present invention relates to a process for the production of (1RS,3RS,6RS)-6-Dimethylaminomethyl-1-(3-methoxy-phenyl)cyclohexane-1,3-diol hydrochloride of crystalline form A comprising precipitating the free base solution of (1RS,3RS,6RS)-6-Dimethylaminomethyl-1-(3-methoxy-phenyl)cyclohexane-1,3-diol with concentrated hydrochloric acid, stirring and filtering off the liquid phase, drying of the solid at 40-60° C., preferred at 45-55° C., and reduced pressure of less than 300 mbar, preferred 150 mbar, for 20-40, preferred 20-28, hours, keeping the temperature at 120-140° C., preferred 125-135° C., for 60-80, preferred 70-74 hours at less than 150 mbar pressure, reducing the temperature to 50-70° C., preferred 55-65° C., and drying the product for another 20-60, preferred 20-30, hours at 50-70, preferred 55-65° C., at less than 150 mbar.

The very preferred process starts from a free base solution of (1RS,3RS,6RS)-6-Dimethylaminomethyl-1-(3-methoxy-phenyl)cyclohexane-1,3-diol, which is precipitated with concentrated hydrochloric acid and allowed to stirr further for 24 hours. The liquid phase is filtered off. The solid is dried at 50°

C.±5° C. and reduced pressure of less than 150 mbar for 24 hours. After that the temperature is kept at 130° C. for another 72±10 hours at less than 150 mbar pressure. Then the temperature is again reduced to 60° C. and the product is dried for another 24 hours at 60° C. and less than 150 mbar. The obtained substance is (1RS,3RS,6RS)-6-Dimethylaminomethyl-1-(3-methoxy-phenyl)cyclohexane-1,3-diol hydrochloride of crystalline form A.

The present invention further relates to crystalline form A of (1RS,3RS,6RS)-6-Dimethylaminomethyl-1-(3-methoxyphenyl)cyclohexane-1,3-diol hydrochloride obtainable by one of the processes described herein.

Crystalline form A of (1RS,3RS,6RS)-6-Dimethylaminomethyl-1-(3-methoxy-phenyl)cyclohexane-1,3-diol hydrochloride has the advantage of having very high solubility in water and may easily be formulated into a medicament. Moreover, since form A is an anhydrous form, the moisture (water) content must not be taken into account during formulation. Moreover form A is resistant to water absorption of up to 60% relative humidity at room temperature for prolonged periods of time, at least up to three weeks. Form A is also stable in organic media such as chloroform, dioxane, ethyl acetate, hexane, tetrahydrofuran, toluene at room temperature or higher temperatures (e.g. up to 40° C.), e.g. in chloroform and hexane.

This invention further relates to a new crystalline form B of (1RS,3RS,6RS)-6-Dimethylaminomethyl-1-(3-methoxyphenyl)cyclohexane-1,3-diol hydrochloride. Crystalline form B can be used as active ingredient in pharmaceutical compositions.

Therefore the invention further relates to a pharmaceutical composition containing as active ingredient (1RS,3RS,6RS)-6-Dimethylaminomethyl-1-(3-methoxy-phenyl)cyclohexane-1,3-diol hydrochloride of crystalline form B according to the invention and at least one suitable additive and/or auxiliary substance.

The most important X-ray lines (2-theta values) in terms of intensity characterizing form B of (1RS,3RS,6RS)-6-Dimethylaminomethyl-1-(3-methoxy-phenyl)cyclohexane-1,3-diol hydrochloride showing one or a combination of the following in a powder diffraction measurement when measured using Cu $K_\alpha$ radiation at ambient temperature are 9.7±0.2, 13.6±0.2, 14.6±0.2, 16.3±0.2, 20.6±0.2 and 29.6±0.2.

To discriminate crystalline form B of (1RS,3RS,6RS)-6-Dimethylaminomethyl-1-(3-methoxy-phenyl)cyclohexane-1,3-diol hydrochloride from the other modifications it is more advantageous to look at the unique peaks in the X-ray diffraction diagram, i.e. the lines with sufficient intensity at 2-theta values, where the other modifications do not show lines with significant intensity. Such characteristic X-ray lines (2-theta values) for form B in a powder diffraction pattern when measured using $CuK_\alpha$ radiation at ambient temperature are: 9.7±0.2, 10.5±0.2, 13.6±0.2, 14.6±0.2, 20.6±0.2, 21.6±0.2, 27.2±0.2 and 29.6±0.2.

RAMAN technique can also be used to identify of the crystalline form B of (1RS,3RS,6RS)-6-Dimethylaminomethyl-1-(3-methoxy-phenyl)cyclohexane-1,3-diol hydrochloride as shown in FIG. 4. Especially the range between 800 cm$^{-1}$ and 200 cm$^{-1}$ is advantageously used also by way of RAMAN microscopy. The most important Raman wave numbers (cm$^{-1}$) in terms of intensity characterizing form B of (1RS,3RS,6RS)-6-Dimethylaminomethyl-1-(3-methoxyphenyl)cyclohexane-1,3-diol hydrochloride showing one or a combination of the following in a Raman spectrum when measured using a laser wave length of 632 nm are 633±4, 720±4, 836±4, 995±4, 1109±4, 1600±4, 2921±4, and 2944±4 cm$^{-1}$.

The present invention further relates to a process for the preparation of crystalline form B of (1RS,3RS,6RS)-6-Dimethylaminomethyl-1-(3-methoxy-phenyl)cyclohexane-1,3-diol hydrochloride comprising the steps of dissolving crystalline form A in ethanol and/or water, sonication and allowing evaporating at room temperature at atmospheric pressure.

In another aspect the present invention relates to a process for the production of (1RS,3RS,6RS)-6-Dimethylaminomethyl-1-(3-methoxy-phenyl)cyclohexane-1,3-diol hydrochloride of crystalline form B comprising the steps of dissolving crystalline form A in ethanol and/or water, preferred ratio range ethanol to water 9, 5:0,5 to 0,5 to 9,5 (weight/weight), very preferred ethanol and water ratio 9:1 (weight/weight), sonication, filtering, and allowing evaporating at room temperature by atmospheric pressure.

The preferred process starts from crystalline form A of (1RS,3RS,6RS)-6-Dimethylaminomethyl-1-(3-methoxyphenyl)cyclohexane-1,3-diol hydrochloride. In one embodiment of the process (1RS,3RS,6RS)-6-Dimethylaminomethyl-1-(3-methoxy-phenyl)cyclohexane-1,3-diol hydrochloride of crystalline form B is produced by dissolving 30-50 mg (1RS,3RS,6RS)-6-Dimethylaminomethyl-1-(3-methoxy-phenyl)cyclohexane-1,3-diol hydrochloride of crystalline form A in a mixture of about 100 μl ethanol and water (w:w; 9:1) of HPLC grade. After sonication to assist dissolution the solution is filtered through a 0.2 micron filter attached to a syringe into a scintillation vial at ambient temperature. The solvent is allowed to evaporate at ambient temperature at athmospheric pressure. The remaining substance is (1RS,3RS,6RS)-6-Dimethylaminomethyl-1-(3-methoxyphenyl)cyclohexane-1,3-diol hydrochloride form B.

Alternatively instead of an ethanol and water (w:w; 9:1) mixture an ethanol and water mixture of w:w; 6:1 and HPLC grade can be used.

Alternatively instead of an ethanol and water (w w; 9:1) mixture water of HPLC grade can be used.

In another aspect the present invention relates to crystalline form B of (1RS,3RS,6RS)-6-Dimethylaminomethyl-1-(3-methoxy-phenyl)cyclohexane-1,3-diol hydrochloride obtainable by a process as described herein.

Crystalline form B (hydrated form) has the advantage that even under high humidity it is not converted to another polymorph. Thus, this crystalline form is particularly suitable for use in wet granulation processes, which are widely used in the pharmaceutical industry.

This invention further relates to a new crystalline form C of (1RS,3RS,6RS)-6-Dimethylaminomethyl-1-(3-methoxyphenyl)cyclohexane-1,3-diol hydrochloride. Crystalline form C can be used as active ingredient in pharmaceutical compositions.

Therefore the invention further relates to a pharmaceutical composition containing as active ingredient (1RS,3RS,6RS)-6-Dimethylaminomethyl-1-(3-methoxy-phenyl)cyclohexane-1,3-diol hydrochloride of crystalline form C according to the invention and at least one suitable additive and/or auxiliary substance.

The most important X-ray lines (2-theta values) in terms of intensity characterizing form C of (1RS,3RS,6RS)-6-Dimethylaminomethyl-1-(3-methoxy-phenyl)cyclohexane-1,3-diol hydrochloride showing one or a combination of the following in a powder diffraction measurement when measured using Cu $K_\alpha$ radiation at ambient temperature are 14.1±0.2, 17.4±0.2, 19.5±0.2, 20.0±0.2, 23.4±0.2 and 26.6±0.2.

To discriminate crystalline form C of (1RS,3RS,6RS)-6-Dimethylaminomethyl-1-(3-methoxy-phenyl)cyclohexane-1,3-diol hydrochloride from the other modifications it is more advantageous to look at the unique peaks in the X-ray diffraction diagram, i.e. the lines with sufficient intensity at 2-theta values, where the other modifications do not show lines with significant intensity. Such characteristic X-ray lines (2-theta values) for form C in a powder diffraction pattern when measured using $CuK_\alpha$ radiation at ambient temperature are: 11.9±0.2, 12.2±0.2, 12.6±0.2, 15.4±0.2, 17.3±0.2, 22.3±0.2, and 23.4±0.2.

RAMAN technique can also be used to identify of the crystalline form C of (1RS,3RS,6RS)-6-Dimethylaminomethyl-1-(3-methoxy-phenyl)cyclohexane-1,3-diol hydrochloride as shown in FIG. 6. The most important Raman wave numbers ($cm^1$) in terms of intensity characterizing form C of (1RS,3RS,6RS)-6-Dimethylaminomethyl-1-(3-methoxy-phenyl)cyclohexane-1,3-diol hydrochloride showing one or a combination of the following in a Raman spectrum when measured using a laser wave length of 632 nm are 239±4, 305±4, 448±4, 502±4, 537±4, 722±4, 830±4, 992±4, 1094±4, 1243±4, 2928±4 and 2945±4 $cm^{-1}$.

The invention further relates to a process for the preparation of crystalline form C of (1RS,3RS,6RS)-6-Dimethylaminomethyl-1-(3-methoxy-phenyl)cyclohexane-1,3-diol hydrochloride comprising the step of dissolving the free base (1RS,3RS,6RS)-6-Dimethylaminomethyl-1-(3-methoxy-phenyl)cyclohexane-1,3-diol in isopropanol at a temperature above room temperature.

In another aspect the present invention relates to a process for the production of (1RS,3RS,6RS)-6-Dimethylaminomethyl-1-(3-methoxy-phenyl)cyclohexane-1,3-diol hydrochloride of crystalline form C comprising the step of dissolving the free base of (1RS,3RS,6RS)-6-Dimethylaminomethyl-1-(3-methoxy-phenyl)cyclohexane-1,3-diol in isopropanol at 40-xx° C., wherein xx is the boiling point of isopropanol under the given conditions (approximately 82° C. under ambient conditions), cooling and treatment of solution with hydrogenchloride.

The very preferred process starts from the free base of (1RS,3RS,6RS)-6-Dimethylaminomethyl-1-(3-methoxy-phenyl)cyclohexane-1,3-diol of crystalline form A. Approximately 20 g are dissolved in isopropanol at an elevated temperature (approximately 45° C. or higher) to reach complete dissolution. The samples were allowed to cool to ambient temperature before treatment with gaseous hydrogen chloride. A constant purge of nitrogen was bubbled through the clear solution while stirring. Anhydrous hydrogen chloride was introduced into the system through the purge stream. Addition of hydrogen chloride was stopped when precipitation was observed. (1RS,3RS,6RS)-6-Dimethylaminomethyl-1-(3-methoxy-phenyl)cyclohexane-1,3-diol hydrochloride form C was recovered by vacuum filtration immediately after formation.

In another aspect the present invention relates to a process for the production of form C comprising the steps of suspending crystalline form A in a liquid medium, stirring the resulting suspension and filtering off the liquid.

The liquid medium may preferably be selected from the group consisting of acetonitrile, a mixture of acetonitrile and water, ethanol, and a mixture of tetrahydrofuran and methanol. The temperature is preferably kept at 15-75° C., more preferably 15-60° C., yet more preferably 20-45° C., most preferably 20-26° C.

In another one of its aspects the present invention relates to crystalline form C of (1RS,3RS,6RS)-6-Dimethylaminomethyl-1-(3-methoxy-phenyl)cyclohexane-1,3-diol hydrochloride obtainable by a process as described herein.

Polymorph C has the advantage that it has the lowest hygroscopicity of all known polymorphic forms. Moreover it has the highest thermodynamic stability of the known polymorphic forms at temperatures of 15-60° C., particulary of 15-35° C. These properties make polymorph C particularly useful for its formulation into a pharmaceutical composition and a medicament.

The thermodynamic properties can be evaluated by measuring the equilibrium solubilities in the respective temperature range such as 15-60° C. and in particular 15-35° C. and graphical evaluation of the results via a van't Hoff Plot (solubility vs. 1/T) as described in the publications of W. Higuchi et al, J. Pharm. Sci. 1963, 52, 150-153 and S. R. Byrn., Solid State Chemistry of drugs, $2^{nd}$ edition, SSCI Inc., 1999. The respective parts of the descriptions are hereby incorporated by reference and form part of the present disclosure.

This invention further relates to a new crystalline form D of (1RS,3RS,6RS)-6-Dimethylaminomethyl-1-(3-methoxy-phenyl)cyclohexane-1,3-diol hydrochloride. Crystalline form D can be used as active ingredient in pharmaceutical compositions.

Therefore the invention further relates to a pharmaceutical composition containing as active ingredient (1RS,3RS,6RS)-6-Dimethylaminomethyl-1-(3-methoxy-phenyl)cyclohexane-1,3-diol hydrochloride of crystalline form D according to the invention and at least one suitable additive and/or auxiliary substance.

The most important X-ray lines (2-theta values) in terms of intensity characterizing form D of (1RS,3RS,6RS)-6-Dimethylaminomethyl-1-(3-methoxy-phenyl)cyclohexane-1,3-diol hydrochloride showing one or a combination of the following in a powder diffraction measurement when measured using Cu $K_\alpha$ radiation at ambient temperature are 17.9±0.2, 18.6±0.2, 19.0±0.2, 19.9±0.2 and 25.7±0.2.

To discriminate crystalline form D of (1RS,3RS,6RS)-6-Dimethylaminomethyl-1-(3-methoxy-phenyl)cyclohexane-1,3-diol hydrochloride from the other modifications it is more advantageous to look at the unique peaks in the X-ray diffraction diagram, i.e. the lines with sufficient intensity at 2-theta values, where the other modifications do not show lines with significant intensity. Such characteristic X-ray lines (2-theta values) for form D in a powder diffraction pattern when measured using $CuK_\alpha$ radiation at ambient temperature are: 10.3±0.2, 12.7±0.2, 13.0±0.2, 13.5±0.2, 18.6±0.2, 25.7±0.2 and 28.7±0.2.

RAMAN technique can also be used to identify of the crystalline form D of (1RS,3RS,6RS)-6-Dimethylaminomethyl-1-(3-methoxy-phenyl)cyclohexane-1,3-diol hydrochloride as shown in FIG. 8.

The Invention further relates to a process for the preparation of crystalline form D of (1RS,3RS,6RS)-6-Dimethylaminomethyl-1-(3-methoxy-phenyl)cyclohexane-1,3-diol hydrochloride comprising the step of heating crystalline form B to a temperature of at least 160° C.

In another aspect the present invention related to a process for the production of (1RS,3RS,6RS)-6-Dinnethylaminomethyl-1-(3-methoxy-phenyl)cyclohexane-1,3-diol hydrochloride of crystalline form D comprising heating form B to 160-1'85° C., preferred 175-185° C., for 20-50, preferred 30-40 minutes, and cooling to room temperature.

The very preferred process starts from the freshly prepared (1RS,3RS,6RS)-6-Dimethylaminomethyl-1-(3-methoxy-phenyl)cyclohexane-1,3-diol hydrochloride form B. A small sample is heated in a XRPD glass capillary to 180° C. for approx. 35 minutes. After cooling down to ambient temperature (1RS,3RS,6RS)-6-Dimethylaminomethyl-1-(3-methoxy-phenyl)cyclohexane-1,3-diol hydrochloride form D was recovered.

Another aspect of the present invention relates to crystalline form D of (1RS,3RS,6RS)-6-Dimethylaminomethyl-1-(3-methoxy-phenyl)cyclohexane-1,3-diol hydrochloride obtainable by a process as described herein.

This invention further relates to a new crystalline form E of (1RS,3RS,6RS)-6-Dimethylaminomethyl-1-(3-methoxy-phenyl)cyclohexane-1,3-diol hydrochloride. Crystalline form E can be used as active ingredient in pharmaceutical compositions.

Therefore the invention further relates to a pharmaceutical composition containing as active ingredient (1RS,3RS,6RS)-6-Dimethylaminomethyl-1-(3-methoxy-phenyl)cyclohexane-1,3-diol hydrochloride of crystalline form E according to the invention and at least one suitable additive and/or auxiliary substance.

The most important X-ray lines (2-theta values) in terms of intensity characterizing form E of (1RS,3RS,6RS)-6-Dimethylaminomethyl-1-(3-methoxy-phenyl)cyclohexane-1,3-diol hydrochloride showing one or a combination of the following in a powder diffraction measurement when measured using Cu $K_\alpha$ radiation at ambient temperature are 9.7±0.2, 14.9±0.2, 16.6±0.2, 19.2±0.2, 21.4±0.2 and 27.3±0.2.

To discriminate crystalline form E of (1RS,3RS,6RS)-6-Dimethylaminomethyl-1-(3-methoxy-phenyl)cyclohexane-1,3-diol hydrochloride from the other modifications it is more advantageous to look at the unique peaks in the X-ray diffraction diagram, i.e. the lines with sufficient intensity at 2-theta values, where the other modifications do not show lines with significant intensity. Such characteristic X-ray lines (2-theta values) for form D in a powder diffraction pattern when measured using $CuK_\alpha$ radiation at ambient temperature are: 10.7±0.2, 14.9±0.2, 21.4±0.2, 22.4±0.2, 24.2±0.2 and 28.9±0.2

RAMAN technique can also be used to identify of the crystalline form E of (1RS,3RS,6RS)-6-Dimethylaminomethyl-1-(3-methoxy-phenyl)cyclohexane-1,3-diol hydrochloride as shown in FIG. 10.

The Invention further relates to a process for the preparation of crystalline form E of (1RS,3RS,6RS)-6-Dimethylaminomethyl-1-(3-methoxy-phenyl)cyclohexane-1,3-diol hydrochloride comprising the step of heating crystalline form B to 80-100° C.

In another aspect the present invention relates to a process for the production of (1RS,3RS,6RS)-6-Dimethylaminomethyl-1-(3-methoxy-phenyl)cyclohexane-1,3-diol hydrochloride of crystalline form E comprising the step of heating form B to 80-100° C., preferred 85-95° C., for 20-40, preferred 25-35, minutes.

The very preferred process starts from the freshly prepared (1RS,3RS,6RS)-6-Dimethylaminomethyl-1-(3-methoxy-phenyl)cyclohexane-1,3-diol hydrochloride form B. A small sample is heated in a XRPD glass capillary to 90° C. for approx. 30 minutes. At this temperature (1RS,3RS,6RS)-6-Dimethylaminomethyl-1-(3-methoxy-phenyl)cyclohexane-1,3-diol hydrochloride form E was recovered. Alternatively form E is prepared by drying freshly prepared (1RS,3RS,6RS)-6-Dimethylaminomethyl-1-(3-methoxy-phenyl)cyclohexane-1,3-diol hydrochloride form B at 60° C. at ambient relative humidity for 2 to 6 weeks. Another aspect of the present invention relates to crystalline form E of (1RS,3RS,6RS)-6-Dimethylaminomethyl-1-(3-methoxy-phenyl)cyclohexane-1,3-diol hydrochloride obtainable by a process as described herein.

The preferred crystalline form is form A.
The preferred crystalline form is form B.
The preferred crystalline form is form C.
The preferred crystalline form is form D.
The preferred crystalline form is form E.

The very preferred crystalline forms are A, B, C especially preferred form is C.

Further objects of the invention are also different mixtures comprising one or more selected from the form A, B, C, D, E.

Further objects of the invention are compositions comprising mixtures of crystalline forms according to the invention, preferred mixtures of crystalline forms comprising one or more members selected from the group of the forms A, B, C, very preferred comprising form C.

Further objects of the invention are pharmaceutical composition containing as active ingredient a or a mixture of, preferred a, crystalline form(s) according to the invention and containing preferred at least one suitable additive and/or auxiliary substance.

Further objects of the invention are the use of a or a mixture of, preferred a, crystalline form(s) according to the invention for the production of a medicament for treating pain. Preferably the pain is selected from the group consisting of acute pain, chronic pain, visceral pain, neuropathic pain and inflammatory pain, more preferably preferred acute or chronic pain.

Pharmaceutical compositions according to the invention may preferably contain in addition to the crystalline forms (1RS,3RS,6RS)-6-Dimethylaminomethyl-1-(3-methoxy-phenyl)cyclohexane-1,3-diol hydrochloride, one or more suitable additive and/or auxiliary substance such as for example carrier materials, fillers, solvents, diluents, colouring agents and/or binders, and may be administered as liquid medicament preparations in the form of injectable solutions, drops or juices; as semi-solid or solid medicament preparations in the form of granules, tablets, pellets, patches, capsules, plasters or aerosols.

The choice of the auxiliary substances, etc., as well as the amounts thereof to be used depend on whether the medicament is to be administered orally, per orally, parenterally, intravenously, intraperitoneally, intradermally, intramuscularly, intranasally, buccally, rectally or topically, for example to the skin, the mucous membranes or the eyes. For oral application suitable preparations are in the form of tablets, sugar-coated pills, capsules, granules, droplets, juices and syrups, while for parenteral, topical and inhalative application suitable forms are solutions, suspensions, readily reconstitutable dry preparations, as well as sprays. The multiparticulate forms such as pellets or crystals may, for example, be compressed into a tablet, filled into a capsule or suspended in a suitable liquid. Crystalline forms in a depot form, in dissolved form or in a plaster, optionally with the addition of agents promoting skin penetration, are suitable percutaneous application preparations. Preparation forms that can be administered orally or percutaneously can provide for the delayed release of crystalline forms according to the invention. In principle further active constituents known to the person skilled in the art may be added to the medicaments/pharmaceutical compositions according to the present invention.

The inventive pharmaceutical formulations/medicaments may be produced using materials, means, devices and processes that are well known in the prior art of pharmaceutical formulations, as described for example in "Remington's Pharmaceutical Sciences", A. R. Gennaro (ed.), $17^{th}$ edition, Mack Publishing Company, Easton, Pa. (1985), in particular in part 8, chapters 76 to 93. The respective parts of the description are hereby incorporated by reference and form part of the disclosure.

The amount of active constituent to be administered to the patient varies depending on the patient's weight, on the type of application, medical indication and severity of the condition. Normally 0.005 to 1000 mg/kg, preferably 0.05 to 5 mg/kg of the crystalline forms according to the invention are administered.

Preferably, the crystalline forms according to the invention are used for the treatment of pain, wherein the pain is preferably selected from the group of chronic pain, acute pain, visceral pain, neuropathic pain and inflammatory pain, more preferably the pain is chronic pain or acute pain.

Additionally the invention relates to a method of treatment using a sufficient amount of the crystalline forms according to the invention for the treatment of a disease, preferably for treating pain, urinary incontinence, depression or anxiety, preferably pain, more preferably pain selected from the group of chronic pain, acute pain, visceral pain, neuropathic pain and inflammatory pain, yet more preferably for the treatment of chronic pain or acute pain.

BRIEF DESCRIPTION OF THE DRAWINGS

FIG. 1 is an X-ray powder diffraction pattern of crystalline form A;
FIG. 2 is a RAMAN spectrum of crystalline form A;
FIG. 3 is an X-ray powder diffraction pattern of crystalline form B;
FIG. 4 is a RAMAN spectrum of crystalline form B;
FIG. 5 is an X-ray powder diffraction pattern of crystalline form C;
FIG. 6 is a RAMAN spectrum of crystalline form C;
FIG. 7 is an X-ray powder diffraction pattern of crystalline form a
FIG. 8 is a RAMAN spectrum of crystalline form D;
FIG. 9 is an X-ray powder diffraction pattern of crystalline form E, and
FIG. 10 is a RAMAN spectrum of crystalline form E.

DESCRIPTION OF EMBODIMENTS

The following Examples shall further illustrate the invention without limiting it thereto.

EXAMPLE 1

Powder Diffraction Patterns of Forms A, B and C

Powder Data Collection was done with a STOE Stadi P Powder Diffractometer equipped with a curved germanium monochromator and a linear position sensitive detector. The samples were prepared as flat samples. As source of the beam a copper X-ray tube with monochromatized Cu K$\alpha_1$ ($\lambda$=1.54051 Å) radiation generated at 50 kV and 30 mA was used. The 2θ area for the measurement was 2°-50°. The used step width was 0.05 degrees. The data were collected at a temperature of 23±1°.

The X-ray powder pattern for form A is shown in FIG. 1, the X-ray powder pattern for form B is shown in FIG. 3 and the X-ray powder pattern for form C is shown in FIG. 5.

The data are shown in Table 1.

EXAMPLE 2

Powder Diffraction Patterns of Forms D and E

Powder Data Collection was carried out on a Shimadzu XRD-6000X-ray powder diffractometer using Cu Kα radiation. The instrument is equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed each day to check the instrument alignment. The data were collected at a temperature of 23±1°.

The X-ray powder diffraction pattern for form D is shown in FIG. 7 and the X-ray powder diffraction pattern for form E is shown in FIG. 9.

The data are shown in Table 1.

TABLE 1

Peak and Relative Intensity Listing
(degree 2θ, peaks with I/I1 value)

| Peak No. | A | I/I1 | B | I/I1 | C | I/I1 | D | I/I1 | E | I/I1 |
|---|---|---|---|---|---|---|---|---|---|---|
| 1 | 12.87 | 35 | 6.43 | 29 | 6.55 | 7 | 10.28 | 9 | 6.76 | 8 |
| 2 | 13.25 | 11 | 9.67 | 46 | 11.89 | 22 | 12.74 | 21 | 9.68 | 35 |
| 3 | 14.08 | 12 | 10.52 | 30 | 12.19 | 26 | 13.02 | 26 | 10.74 | 18 |
| 4 | 14.28 | 18 | 12.57 | 17 | 12.58 | 26 | 13.54 | 18 | 13.96 | 16 |
| 5 | 15.77 | 14 | 13.61 | 64 | 12.97 | 20 | 13.7 | 21 | 14.50 | 11 |
| 6 | 16.09 | 9 | 14.24 | 42 | 14.05 | 46 | 14.1 | 20 | 14.94 | 24 |
| 7 | 16.62 | 23 | 14.64 | 70 | 14.93 | 17 | 15.78 | 21 | 16.62 | 21 |
| 8 | 17.53 | 30 | 16.34 | 52 | 15.39 | 19 | 16.24 | 10 | 17.52 | 10 |
| 9 | 17.92 | 27 | 17.05 | 23 | 15.89 | 13 | 17.5 | 15 | 17.90 | 10 |
| 10 | 18.95 | 79 | 17.54 | 58 | 16.35 | 17 | 17.94 | 40 | 19.20 | 20 |
| 11 | 19.29 | 100 | 19.34 | 20 | 17.25 | 29 | 18.6 | 66 | 20.44 | 15 |
| 12 | 20.04 | 21 | 20.36 | 29 | 17.44 | 55 | 19.04 | 100 | 21.38 | 100 |
| 13 | 20.38 | 10 | 20.64 | 100 | 18.34 | 20 | 19.90 | 50 | 23.28 | 13 |
| 14 | 21.01 | 47 | 21.06 | 83 | 19.47 | 100 | 20.4 | 18 | 24.18 | 19 |
| 15 | 21.99 | 8 | 21.61 | 40 | 19.96 | 58 | 21.1 | 17 | 25.16 | 12 |
| 16 | 23.84 | 8 | 22.06 | 33 | 21.14 | 48 | 21.92 | 10 | 25.18 | 12 |
| 17 | 24.68 | 17 | 23.17 | 23 | 22.27 | 15 | 23.58 | 23 | 25.20 | 10 |
| 18 | 25.28 | 40 | 23.56 | 23 | 22.84 | 9 | 25.3 | 19 | 25.22 | 11 |
| 19 | 25.83 | 9 | 23.92 | 15 | 23.37 | 40 | 25.7 | 34 | 25.24 | 11 |
| 20 | 25.99 | 10 | 24.57 | 19 | 23.85 | 16 | 27.2 | 20 | 26.70 | 12 |
| 21 | 27.20 | 7 | 25.75 | 28 | 24.44 | 25 | 27.8 | 22 | 27.26 | 24 |
| 22 | 27.76 | 12 | 26.31 | 17 | 25.22 | 16 | 28.7 | 22 | 28.86 | 17 |
| 23 | 29.38 | 11 | 26.80 | 16 | 26.15 | 14 | 30.5 | 24 | 30.12 | 34 |
| 24 | 29.85 | 13 | 27.16 | 39 | 26.58 | 47 | 31.7 | 11 | 32.34 | 19 |
| 25 | 30.64 | 12 | 28.31 | 16 | 30.02 | 21 | 32.4 | 10 | 37.80 | 13 |
| 26 | 31.34 | 9 | 29.18 | 36 | 31.04 | 15 | 33.1 | 22 | 38.94 | 15 |
| 27 | 31.83 | 10 | 29.58 | 55 | 32.16 | 10 | 33.6 | 18 | | |
| 28 | 32.38 | 6 | 31.49 | 24 | 32.58 | 16 | 36.8 | 15 | | |
| 29 | 33.02 | 16 | 31.69 | 43 | 33.44 | 16 | 38.4 | 11 | | |
| 30 | 33.50 | 16 | 32.03 | 29 | 34.98 | 12 | 10.28 | 9 | | |
| 31 | | | 34.44 | 13 | 36.98 | 8 | | | | |
| 32 | | | 36.94 | 12 | 37.29 | 10 | | | | |

EXAMPLE 3

RAMAN Spectra of Forms A, B and C

The polymorphs of (1RS,3RS,6RS)-6-Dimethylaminomethyl-1-(3-methoxy-phenyl)cyclohexane-1,3-diol hydrochloride were investigated using RAMAN microscopy. The RAMAN spectrometer used was a Jobin Yvon Horiba Labram. The microscope was an Olympus BX40 System, 100×Obj., diode laser 632 nm. Raman microscopy was able to distinguish between forms A, B, C and D. Differences between the spectra of the two forms appear in the whole spectral range (3500-150 cm$^{-1}$).

The results for form A are shown in FIG. 2, the results for form B in FIG. 4, the results for form C in FIG. 6.

EXAMPLE 4

RAMAN Spectra of Forms D and E

The polymorphs of (1RS,3RS,6RS)-6-Dimethylaminomethyl-1-(3-methoxy-phenyl)cyclohexane-1,3-diol hydrochloride were investigated using RAMAN spectroscopy The Raman spectrum was acquired on a Raman accessory interfaced to a Nicolet Magna 960 Fourier transform infrared spectrometer using InGaAs detector. The accessory utilizes an excitation wavelength of 1064 nm and approximately 0.45 W of Nd:YAG laser power. The spectrum represents 256 co-added scans acquired at 4 cm$^{-1}$ resolution. The sample was prepared for analysis by placing a portion into a 5-mm diameter glass tube and positioning this tube in the spectrometer. The spectrometer was calibrated (wavelength) with sulfur and cyclohexane at the time of use.

The results for form D are shown in FIG. 8, the results for form E in FIG. 10.

EXAMPLE 5

Variable Temperature X-Ray Powder Diffraction Experiment

Variable temperature Powder Diffraction Data Collection was carried out on a Shimadzu XRD-6000X-ray powder diffractometer using Cu Kα radiation. The instrument is equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2,5 to 40° 2 θ was used. A silicon standard was analyzed each day to check the instrument alignment. The instrument was equipped with an Anton Paar HTK 1200 high temperature stage and a ceramic sample holder A variable temperature X-ray powder diffraction experiment was run thereby producing form E from form B. form B converted to form E at 90° C. after half an hour during the experiment.

EXAMPLE 6

Several milligrams of crystalline form A were suspended in acetonitrile at room temperature and stirred at this temperature for several hours. The thus obtained residue of crystalline form C was filtered off.

EXAMPLE 7 a)
Several milligrams of crystalline form A were suspended in a mixture of acetonitrile and water (99:1 weight/weight) at room temperature and stirred at this temperature for several hours. The thus obtained residue of crystalline form C was filtered off
b)
Crystalline form C was also obtained when the process was carried out at 60° C.

EXAMPLE 8 a)
Several milligrams of crystalline form A were suspended in ethanol at room temperature and stirred at this temperature for several hours. The thus obtained residue of crystalline form C was filtered off.
b)
Crystalline form C was also obtained when the process was carried out at 60° C.

EXAMPLE 9

Several milligrams of crystalline form A were suspended in a mixture of tetrahydrofuran and methanol (95:5 weight/weight) at room temperature and stirred at this temperature for several hours. The thus obtained residue of crystalline form C was filtered off.

EXAMPLE 10

Crystalline form B in an open glas container is stored in a humidity chamber at relative humidity of 35% and room temperature. Samples were taken prior to storage and after 4, 14, 19 and 21 days of storage under these conditions. In all cases the samples were found to be crystalline form B only.

EXAMPLE 11

Crystalline form B in an open glas container is stored in a humidity chamber at relative humidity of 60% and room temperature. Samples were taken prior to storage and after 7, 17 and 22 days of storage under these conditions. In all cases the samples were found to be crystalline form B only.

EXAMPLE 12

Crystalline form B in an open glas container is stored in a humidity chamber at relative humidity of 75% and room temperature. Samples were taken prior to storage and after 6, 13 and 23 days of storage under these conditions. In all cases the samples were found to be crystalline form B only.

EXAMPLE 13

Several milligrams of crystalline form A were suspended in mixtures of ethanol and water (95:5; 61.5:1; 18.3:1, 8.3:1, 3.8:1 and 1:2.8, in each case weight/weight) at room temperature and stirred at this temperature for several hours. Subsequently the ethanol/water mixture is removed under reduced pressure. The thus obtained residue of crystalline form B was filtered off.

The invention claimed is:

1. A crystalline form of (1RS,3RS,6RS)-6-dimethylaminomethyl-1-(3-methoxy-phenyl)cyclohexane-1,3-diol hydrochloride selected from the group consisting of:
   a) crystalline form A which exhibits the 2-theta values 12.9±0.2, 17.5±0.2, 19.0±0.2, 19.3±0.2, 21.0±0.2 and 25.3±0.2 for powder diffraction X-ray lines measured using Cu Kα radiation;
   b) crystalline form C which exhibits the 2-theta values 14.1±0.2, 17.4±0.2, 19.5±0.2, 20.0±0.2, 23.4±0.2 and 26.6±0.2 for powder diffraction X-ray lines measured using Cu Kα radiation;
   c) crystalline form D which exhibits the 2-theta values 17.9±0.2, 18.6±0.2, 19.0±0.2, 19.9±0.2 and 25.7±0.2 for powder diffraction X-ray lines measured using Cu Kα radiation; and
   d) crystalline form E which exhibits the 2-theta values 9.7±0.2, 14.9±0.2, 16.6±0.2, 19.2±0.2, 21.4±0.2 and 27.3±0.2 for powder diffraction X-ray lines measured using Cu Kα radiation.

2. A crystalline form of (1RS,3RS,6RS)-6-dimethyl-aminomethyl-1-(3-methoxy-phenyl)cyclohexane-1,3-diol hydrochloride according to claim 1, wherein said crystalline form is crystalline form A and additionally exhibits the 2-theta values 11.0±0.2, 12.3±0.2, 16.6±0.2 and 17.9±0.2 for powder diffraction X-ray lines measured using Cu Kα radiation.

3. A crystalline form of (1RS,3RS,6RS)-6-dimethyl-aminomethyl-1-(3-methoxy-phenyl)cyclohexane-1,3-diol hydrochloride according to claim 1, wherein said crystalline form is crystalline form A and exhibits an X-ray diffraction pattern measured using Cu Kα radiation essentially as shown in FIG. 1.

4. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form A and exhibits RAMAN spectrum bands measured using a laser wavelength of 632 nm at 227±4, 262±4, 643±4, 716±4, 813±4, 830±4, 970±4, 993±4, 1252±4, 2973±4 and 3273±4 cm$^{-1}$.

5. A crystalline form of (1RS,3RS,6RS)-6-dimethyl-aminomethyl-1-(3-methoxy-phenyl)cyclohexane-1,3-diol hydrochloride according to claim 1, wherein said crystalline form is crystalline form A and exhibits a RAMAN spectrum measured using a laser wavelength of 632 nm essentially as shown in FIG. 2.

6. A process for producing crystalline form A of (1RS,3RS,6RS)-6-dimethylaminomethyl-1-(3-methoxy-phenyl)cyclohexane-1,3-diol hydrochloride according to claim 1, said process comprising:
providing a free base solution of (1RS,3RS,6RS)-6-dimethylaminomethyl-1-(3-methoxy-phenyl) cyclohexane-1 3-diol;
adding hydrochloric acid to said solution to precipitate a hydrochloride salt of (1RS,3RS,6RS)-6-dimethylaminomethyl-1-(3-methoxy-phenyl)cyclohexane -1,3-diol and isolating the precipitated salt in solid form;
initially drying the isolated solid salt at 40-60° C. and a reduced pressure of less than 300 mbar for from 20 to 40, hours;
then maintaining the temperature at 120-140° C. for about 60 to about 80 hours at a pressure of less than 150 mbar; and
thereafter reducing the temperature to 50-70° C., and further drying the salt for another 20 to 60 hours at 50-70° C. and a pressure of less than 150 mbar.

7. A process according to claim 6, wherein;
the solid salt is isolated by stirring and then filtering off the solution after addition of the hydrochloric acid;
the initial drying is effected at 45-55° C., and a reduced pressure of less than 150mbar for 20 to 28, hours;
the temperature is maintained at 125-135° C. for 60 to 80, hours at less than 150mbar pressure; and
the further drying is effected at a reduced temperature of 55-65° C. for another 20 to 30 hours at less than 150 mbar.

8. A process according to claim 7, wherein:
the added hydrochloric acid is concentrated hydrochloric acid, and stirring is carried out for 24 hours prior to filtering off the solution;
the initial drying is effected for 24 hours;
the temperature is maintained at 130° C. for 70 to 74 hours; and
the further drying is effected at a reduced temperature of 60° C. for another 24hours at less than 150 mbar.

9. Crystalline form A of (1RS,3RS,6RS)-6-dimethyl-aminomethyl-1-(3-methoxy-phenyl)cyclohexane-1,3-diol hydrochloride obtained by the process of claim 6.

10. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form C, and additionally exhibits the 2-theta values 11.9±0.2, 12.2±0.2, 12.6±0.2, 15.4±0.2, 17.3±0.2 and 22.3±0.2 for powder diffraction X-ray lines measured using Cu Kα radiation.

11. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form C, and exhibits an X-ray diffraction pattern measured using Cu Kα radiation essentially as shown in FIG. 5.

12. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form C and exhibits RAMAN spectrum bands measured using a laser wavelength of 632 nm at 239±4, 305±4, 448±4, 502±4, 537±4, 722±4, 830±4, 992±4, 1094±4, 1243±4, 2928±4 and 2945±4 cm$^{-1}$.

13. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form C and exhibits a RAMAN spectrum measured using a laser wavelength of 632 nm essentially as shown in FIG. 6.

14. A process for producing crystalline form C of (1RS,3RS,6RS)-6-dimethylaminomethyl-1-(3-methoxy-phenyl)cyclohexane-1, 3-diol hydrochloride according to claim 1, said process comprising:
providing a solution by dissolving (1RS,3RS,6RS)-6-dimethylaminomethyl-1-(3-methoxy-phenyl) cyclohexane-1,3-diol in free base form in isopropanol at a temperature above room temperature;
treating the solution with hydrogen chloride, and
recovering crystalline form C of (1RS,3RS,6RS)-6-dimethylaminomethyl-1-(3-methoxy-phenyl)cyclohexane-1,3-diol hydrochloride.

15. A process according to claim 14, wherein the free base of (1RS,3RS,6RS)-6-dimethylaminomethyl-1-(3-methoxy-phenyl)cyclohexane -1,3-diol is dissolved in isopropanol at a temperature of 40° C. to the boiling point of isopropanol, and the solution is cooled before treating the solution with hydrogen chloride.

16. A process according to claim 15, wherein the free base of (1RS,3RS,6RS)-6-dimethylaminomethyl-1-(3-methoxy-phenyl)cyclohexane-1,3-diol is dissolved in isopropanol at a temperature of 45° C. to the boiling point of isopropanol; and the solution is cooled to ambient temperature and then treated with gaseous anhydrous hydrogen chloride.

17. A process for producing crystalline form C of (1RS,3RS,6RS)-6-dimethylaminomethyl-1-(3-methoxy-phenyl)cyclohexane-1,3-diol hydrochloride according to claim 1, said process comprising:
suspending crystalline form A of (1RS,3RS,6RS)-6-dimethylaminomethyl-1-(3-methoxy-phenyl) cyclohexane-1,3-diol hydrochloride in a liquid medium at a temperature of 15-75° C.;
stirring the suspension for a period of time, and
filtering crystalline form C of (1RS,3RS,6RS)-6-dimethylaminomethyl-1-(3-methoxy-phenyl) cyclohexane-1,3-diol hydrochloride from the stirred suspension.

18. A process according to claim 17, wherein the liquid medium is at a temperature of 20-45° C. and is selected from the group consisting of acetonitrile, a mixture of acetonitrile and water, ethanol, and a mixture of tetrahydrofuran and methanol.

19. Crystalline form C of (1RS,3RS,6RS)-6-dimethyl-aminomethyl-1-(3-methoxy-phenyl)cyclohexane -1,3-diol hydrochloride obtained by the process of claim 14.

20. Crystalline form C of (1RS,3RS,6RS)-6-dimethyl-aminomethyl-1-(3-methoxy-phenyl)cyclohexane -1,3-diol hydrochloride obtained by the process of claim 17.

21. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form D and additionally exhibits the 2-theta values 10.3±0.2, 12.7±0.2, 13.0±0.2, 13.5±0.2 and 28.7±0.2 for powder diffraction X-ray lines measured using Cu Kα radiation.

22. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form D and exhibits an X-ray diffraction pattern measured using Cu Kα radiation essentially as shown in FIG. 7.

23. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form D and exhibits a RAMAN spectrum measured using a laser wavelength of 632 nm essentially as shown in FIG. 8.

24. A process for producing crystalline form D of (1RS, 3RS,6RS)-6-dimethylaminomethyl-1-(3-methoxy-phenyl)cyclohexane-1,3-diol hydrochloride according to claim 1, said process comprising heating crystalline form B of (1RS, 3RS,6RS)-6-dimethylaminomethyl-1-(3-methoxy-phenyl)cyclohexane-1,3-diol hydrochloride to a temperature of at least 160° C.

25. A process according to claim 24, wherein the crystalline form B is heated to 160-185° C. for 20 to 50 minutes and then cooled.

26. A process according to claim 25, wherein the crystalline form B is heated to 175-185° C. for 30 to 40 minutes and then cooled to room temperature.

27. Crystalline form D of (1RS,3RS,6RS)-6-dimethylaminomethyl-1-(3-methoxy-phenyl)cyclohexane-1,3-diol hydrochloride obtained by the process of claim 24.

28. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form E and additionally exhibits the 2-theta values 10.7±0.2, 14.9±0.2, 21.4±0.2, 22.4±0.2, 24.2±0.2 and 28.9±0.2 for powder diffraction X-ray lines measured using Cu Kα radiation.

29. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form E and exhibits an X-ray diffraction pattern measured using Cu Kα radiation essentially as shown in FIG. 9.

30. A crystalline form of (1RS,3RS,6RS)-6-dimethylamino-methyl-1-(3-methoxy-phenyl)cyclohexane-1,3-diol hydrochloride according to claim 1, wherein said crystalline form is crystalline form E and exhibits a RAMAN spectrum measured using a laser wavelength of 632 nm essentially as shown in FIG. 10.

31. A process for producing crystalline form E of (1RS, 3RS,6RS)-6-dimethylaminomethyl-1-(3-methoxy-phenyl)cyclohexane-1,3-diol hydrochloride according to claim 1, said process comprising heating crystalline form B of (1RS, 3RS,6RS)-6-dimethylaminomethyl-1-(3-methoxy-phenyl)cyclohexane-1,3-diol hydrochloride to a temperature of 80-100° C. for 20 to 40 minutes.

32. A process according to claim 31, wherein the crystalline form B is heated to a temperature of 85-95° C. for 25 to 35 minutes.

33. A process for producing crystalline form E of (1RS, 3RS,6RS)-6-dimethylaminomethyl-1-(3-methoxy-phenyl)cyclohexane-1,3-diol hydrochloride according to claim 1, said process comprising drying crystalline form B at 60° C. at ambient relative humidity for 2 to 6 weeks.

34. A process according to claim 33, wherein the crystalline form B is freshly prepared.

35. Crystalline form E of (1RS,3RS,6RS)-6-dimethylaminomethyl-1-(3-methoxy-phenyl)cyclohexane-1,3-diol hydrochloride obtained by the process of claim 31.

36. Crystalline form E of (1RS,3RS,6RS)-6-dimethyl-aminomethyl-1-(3-methoxy-phenyl)cyclohexane-1,3-diol hydrochloride obtained by the process of claim 33.

37. A composition comprising a mixture of at least two crystalline forms of (1RS,3RS,6RS)-6-dimethylaminomethyl-1-(3-methoxy-phenyl) cyclohexane-1,3-diol hydrochloride selected from the group consisting of crystalline forms A through E according to claim 1.

38. A composition according to claim 37, wherein said composition comprises crystalline form A of (1RS,3RS, 6RS)-6-dimethylamino-methyl-1-(3-methoxy-phenyl)cyclohexane-1,3-diol hydrochloride.

39. A pharmaceutical composition comprising at least one crystalline form of (1RS,3RS,6RS)-6-dimethylaminomethyl-1-(3-methoxy-phenyl) cyclo-hexane-1,3-diol hydrochloride according to claim 1 and a pharmaceutically acceptable carrier or auxiliary.

40. A method of treating or inhibiting a condition selected from the group consisting of pain, urinary incontinence, depression and anxiety in a patient, said method comprising administering to said patient a pharmaceutically effective amount of at least one crystalline form of (1RS,3RS,6RS)-6-dimethylaminomethyl-1-(3-methoxy-phenyl)cyclohexane-1,3-diol hydrochloride according to claim 1.

41. A method according to claim 40, wherein said condition is pain selected from the group consisting of chronic pain, acute pain, neuropathic pain, visceral pain, and inflammatory pain.

* * * * *